United States Patent
Liu et al.

(10) Patent No.: US 10,934,408 B2
(45) Date of Patent: Mar. 2, 2021

(54) SURFACE MODIFICATION METHOD FOR POLYETHER-ETHER-KETONE MATERIAL

(71) Applicant: SHANGHAI INSTITUTE OF CERAMICS, CHINESE ACADEMY OF SCIENCES, Shanghai (CN)

(72) Inventors: Xuanyong Liu, Shanghai (CN); Tao Lu, Shanghai (CN); Heying Wang, Shanghai (CN); Fanhao Meng, Shanghai (CN)

(73) Assignee: SHANGHAI INSTITUTE OF CERAMICS, CHINESE ACADEMY OF SCIENCES, Shanghai (CN)

(*) Notice: Subject to any disclaimer, the term of this patent is extended or adjusted under 35 U.S.C. 154(b) by 236 days.

(21) Appl. No.: 15/302,153

(22) PCT Filed: Mar. 18, 2015

(86) PCT No.: PCT/CN2015/074510
§ 371 (c)(1),
(2) Date: Oct. 5, 2016

(87) PCT Pub. No.: WO2015/154613
PCT Pub. Date: Oct. 15, 2015

(65) Prior Publication Data
US 2017/0121479 A1    May 4, 2017

(30) Foreign Application Priority Data

Apr. 9, 2014 (CN) .......................... 201410141117.1
Nov. 17, 2014 (CN) .......................... 201410654364.1

(51) Int. Cl.
C08J 7/14    (2006.01)
C08J 7/12    (2006.01)
(Continued)

(52) U.S. Cl.
CPC ............... *C08J 7/123* (2013.01); *A61L 27/18* (2013.01); *C08J 5/042* (2013.01); *C08J 7/12* (2013.01);
(Continued)

(58) Field of Classification Search
CPC ..... C08J 7/12; C08J 7/123; C08J 7/126; C08J 7/14; C08J 5/005; C08J 5/042;
(Continued)

(56) References Cited

U.S. PATENT DOCUMENTS 4,898,991 A * 2/1990 Huang .................. C07C 43/126
                                                          228/234.2
5,300,683 A * 4/1994 Bierschenk ............. C07C 41/48
                                                             562/582
(Continued)

FOREIGN PATENT DOCUMENTS

| CN | 102330051 A | 1/2012 |
| CN | 103483610 A | 1/2014 |
| CN | 103614699 A | 3/2014 |

OTHER PUBLICATIONS

Rui Ma et al.; "Current Strategies to Improve the Bioactivity of PEEK"; International Journal of Molecular Sciences; vol. 15 pp. 5426-5445; Mar. 28, 2014.*
(Continued)

*Primary Examiner* — Marianne L Padgett
(74) *Attorney, Agent, or Firm* — Alleman Hall Creasman & Tuttle LLP

(57) ABSTRACT

The present invention relates to a surface modification method for a polyether-ether-ketone material. The method combines physical and chemical methods, and comprises the steps of performing plasma immersion ion implantation on the surface of the polyether-ether-ketone material with argon as an ion source, and then, soaking the polyether-ether-
(Continued)

ketone material treated by plasma immersion ion implantation in a hydrogen peroxide aqueous solution, hydrofluoric acid aqueous solution, or ammonia water to make the surface of the modified polyether-ether-ketone material have nanoparticles, shallow nanoporous structures, and/or ravined nanostructures.

2 Claims, 7 Drawing Sheets

(51) Int. Cl.
    *C08J 5/04*            (2006.01)
    *A61L 27/18*        (2006.01)

(52) U.S. Cl.
    CPC ............. *C08J 7/126* (2013.01); *C08J 7/14* (2013.01); *A61L 2400/18* (2013.01); *A61L 2430/02* (2013.01); *C08J 2371/00* (2013.01); *C08J 2371/10* (2013.01)

(58) Field of Classification Search
    CPC ... C08J 2371/00; C08J 2371/10; C08L 77/12; A61L 27/14; A61L 27/16; A61L 27/18; A61L 27/34; A61L 2400/18; A61L 2430/02
    USPC ...... 427/2.24, 2.26, 525, 533, 534, 536, 539; 216/87, 94
    See application file for complete search history.

(56) References Cited

U.S. PATENT DOCUMENTS

| | | | | |
|---|---|---|---|---|
| 5,539,059 | A * | 7/1996 | Bierschenk | C08G 65/3236 204/157.95 |
| 6,464,889 | B1 * | 10/2002 | Lee | A61L 27/3839 204/192.32 |
| 10,407,556 | B2 * | 9/2019 | Cerruti | C08F 120/18 |
| 10,428,455 | B2 * | 10/2019 | Gladish | D06P 5/2011 |
| 2003/0134100 | A1 * | 7/2003 | Mao | A61L 27/34 428/304.4 |
| 2003/0171239 | A1 * | 9/2003 | Patel | C11D 3/0094 510/406 |
| 2006/0138399 | A1 * | 6/2006 | Itano | C11D 7/08 257/40 |
| 2006/0147629 | A1 * | 7/2006 | Wang | B82Y 30/00 427/249.1 |
| 2007/0209200 | A1 * | 9/2007 | Ohmi | G03F 7/40 29/846 |
| 2008/0095816 | A1 * | 4/2008 | Gordy | A61L 27/26 424/422 |
| 2009/0305381 | A1 * | 12/2009 | Bilek | A61L 17/005 435/180 |
| 2010/0086785 | A1 * | 4/2010 | Perry | B29C 70/64 428/412 |
| 2010/0167168 | A1 * | 7/2010 | Kim | C09D 7/62 429/495 |
| 2010/0227372 | A1 * | 9/2010 | Bilek | A61L 27/34 435/180 |
| 2011/0270356 | A1 * | 11/2011 | McKenzie | A61N 1/375 607/57 |
| 2012/0009341 | A1 * | 1/2012 | Noh | A61L 27/04 427/180 |
| 2012/0010599 | A1 * | 1/2012 | Jin | C08L 23/02 604/890.1 |
| 2013/0199539 | A1 * | 8/2013 | Webster | C12N 1/36 128/207.14 |
| 2014/0287945 | A1 * | 9/2014 | Lau | G01N 33/54353 506/9 |
| 2015/0274891 | A1 * | 10/2015 | Konradi | B01D 65/08 210/500.32 |
| 2016/0215111 | A1 * | 7/2016 | Bilek | A61L 27/54 |
| 2017/0007743 | A1 * | 1/2017 | Hedrick | C23C 22/78 |
| 2017/0274123 | A1 * | 9/2017 | Rosell Gratacos | B05D 1/36 |
| 2020/0237965 | A1 * | 7/2020 | Hedrick | C25D 11/02 |

OTHER PUBLICATIONS

JH Wang; "Surface preparation techniques for biomedical applications"; chapter 5 in Coatings for Biomedical Applications; pp. 143-175; Woodhead publishing Limited, 2012.*

Lucie Bacakova et al.; "Nanocomposite and Nanostructured Carbon-based Films as Growth Substrates for Bone Cells"; Chapter 16 of Advances in Diverse Industrial Applications of NanoComposites; pp. 371-408; Intech Open; Mar. 2011.*

KY Law; "Definitions for Hydrophilicity, Hydrophobicity, and Superhydrophobicity: Getting the Basics Right"; the Journal of Physical Chemistry; Letters; ACS publications; Feb. 20, 2014; pp. 686-688.*

Kurtz, S. et al., "PEEK biomaterials in trauma, orthopedic, and spinal implants," Biomaterials, vol. 28, No. 32, Nov. 2007, Available Online Aug. 7, 2007, 25 pages.

Zhao, Y. et al., "Cytocompatibility, osseointegration, and bioactivity of three-dimensional porous and nanostructured network on polyetheretherketone," Biomaterials, vol. 34, No. 37, Dec. 2013, Available Online Sep. 14, 2013, 14 pages.

Wang, H. et al., "Enhanced osteoblast responses to poly ether ether ketone surface modified by water plasma immersion ion implantation," Colloids and Surfaces B: Biointerfaces, vol. 117, May 1, 2014, Available Online Feb. 18, 2014, 9 pages.

ISA State Intellectual Property Office of the People's Republic of China, International Search Report Issued in Application No. PCT/CN2015/074510, Jun. 17, 2015, WIPO, 5 pages.

Liu, "Progress in Research on the Surface/Interface of Materials for Hard Tissue Implant," Journal of Inorganic Materials, vol. 26, No. 1, Jan. 15, 2011, 11 pages, Untranslated Japanese language article, with English abstract.

* cited by examiner

SURFACE MODIFICATION METHOD FOR POLYETHER-ETHER-KETONE MATERIAL

FIELD OF THE INVENTION

The present invention relates to a method for surface modifying polyether-ether-ketone (PEEK) through a plasma immersion ion implantation technique which belongs to the technical field of surface modification of biomedical polymers.

BACKGROUND OF THE INVENTION

PEEK has similar elastic modulus to that of cortical bones, which, after implantation, can mitigate concerns over the risks of osteanabrosis and bone resorption caused by stress shielding. In addition to its excellent mechanical properties, non-toxicity and good chemical resistance make PEEK suitable as a material for biomedical implants for long-term implantation (Biomaterials 2007, 28:4845-4869). Unfortunately, despite the above attractive properties, PEEK is normally bioinert thus impeding osteointegration in vivo after implantation, which limits its long-term application as an implant material. So far several approaches have been developed to improve the inherent poor biocompatibility of PEEK. For instance, formation of composite materials by incorporating bioactive materials (tricalcium phosphate (TCP) and hydroxyapatite (HA)) into a PEEK matrix is an effective way to enhance biocompatibility whereas the mechanical properties are sacrificed to a large extent, thus not conducive to clinical application. Furthermore, using bioactive coatings ($TiO_2$ and HA coatings) is an effective way to preserve the inherent mechanical properties of PEEK. However, the bonding strength between coating and substrate would be a critical problem in a clinic. In addition, although grafting bioactive functional groups (—COOH and —$NH_2$) is an effective method in surface modification for PEEK, the multi-step synthesis process is tedious in operation and time-consuming.

Due to its inherent chemical stability, PEEK possesses the ability to resist corrosion by most chemical reagents except concentrated sulfuric acid (Biomaterials 2013, 34:9264-9277). Therefore, how to simply and effectively enhance biocompatibility while preserving the excellent mechanical properties of PEEK is becoming a topic of great interest worldwide.

SUMMARY OF THE INVENTION

In light of the problem the PEEK material has, an objective of this invention is to provide a simple and effective method to enhance the biocompatibility of PEEK while preserving the inherent properties. In this respect, the invention provides a PEEK material obtained by the plasma immersion ion implantation technique and a method to surface modify the PEEK material.

This invention provides a surface modification method for PEEK materials, which is a combination of a physical method and a chemical method, comprising the steps of: performing plasma immersion ion implantation (PIII) on the surface of the PEEK material with an Ar plasma source; and immersing the plasma immersion ion implantation modified PEEK material in a hydrogen peroxide ($H_2O_2$) aqueous solution, a hydrofluoric acid (HF) aqueous solution, or an ammonia ($NH_3 \cdot H_2O$) solution, in order to form nanoparticles, shallow nanoporous structures, and/or ravined nanostructures in the surface of the PEEK material.

Preferably, the parameters of the PIII process include: a background vacuum pressure of $1 \times 10^{-4} \sim 1 \times 10^{-2}$ Pa, preferably $3 \times 10^{-3} \sim 5 \times 10^{-3}$ Pa, an Ar gas flow of 5~200 sccm, preferably 15~60 sccm, an implantation voltage of 100~2000 V, preferably 500~1000 V, a radio frequency power of 100~2000 W, preferably 300~500 W, an implantation pulse frequency of 30 kHz, a duty ratio of 15~30%, preferably 30%, and an implantation duration of 180 min or shorter, preferably 30~90 min.

Preferably, the parameters of the PIII process include: an Ar gas flow of 30 sccm, an implantation voltage of 800 V, a radio frequency power of 300 W, and an implantation duration of 60 min, while the $H_2O_2$ concentration is 30 wt %, and the immersion duration is 24 h.

Preferably, the $H_2O_2$ concentration is 30 wt % or less, preferably 15~30 wt %, especially 30 wt %, the immersion duration is 6~24 h, preferably 24 h. The HF concentration is 20~40 wt %, the immersion duration is 6~24 h, preferably 24 h. The ammonia concentration is 5~40 wt %, preferably 20~40 wt %, the immersion duration is 6~24 h, preferably 24 h.

Preferably, a shallow nanoporous structure and —OH functional groups are formed on the surface of PIII modified PEEK after the immersion treatment in $H_2O_2$ solution.

Preferably, a ravined nanostructure and nanoparticles are formed on the surface of PIII modified PEEK after the immersion treatment in a HF solution. In addition, fluorine is introduced onto the PIII modified PEEK surface and the fluorine concentration is 20 at % or less, preferably 3.06~9.01 at %.

Preferably, the ravined structure and —$NH_2$ functional groups are formed on the surface of the PIII modified PEEK after the immersion treatment in the ammonia solution.

Preferably, the PEEK material is pure PEEK or carbon fiber reinforced PEEK.

Preferably, the size of the ravined nanostructure is 1~500 nm. In preferable examples, the water contact angle of the modified PEEK surface is 32°~49°. In an example, the fluorine concentration of the modified PEEK surface is 9.01 at % and the water contact angle is 32°.

The method of this invention includes exposing the PEEK surface to Ar gas plasma immersion ion implantation (Ar-PIII) immediately followed by the immersion treatment in a $H_2O_2$ solution, HF solution, or ammonia solution. Nanostructures are formed on the PEEK surface modified according to this invention. For example, the F concentration can reach up to about 9.01 at % after the immersion treatment in a HF solution. The bio-related properties of a fluorinated PEEK surface are greatly enhanced. Cell proliferation evaluation results confirmed that rat bone marrow mesenchymal stem cells (BMSCs) on the modified PEEK surface show a higher proliferation rate than that on an unmodified PEEK surface. In addition, the alkaline phosphatase (ALP) activity of BMSCs incubated for 14 days was up-regulated on the modified PEEK surface, indicating that the modified surface can promote osteogenic differentiation of BMSCs. In addition, antibacterial test results demonstrated that the fluorinated PEEK surface exhibits certain antibacterial effects to *Staphylococcus aureus*. Therefore, this invention can be applied to improve both biocompatibility and antibacterial activity of a medical PEEK material.

BRIEF DESCRIPTION OF THE DRAWINGS

FIG. 1 shows the scanning electron microscopy (SEM) morphologies of unmodified PEEK surface, modified PEEK surface by means of an exemplary method provided herein, and PEEK surface treated by means of another method.

FIG. 2 shows the water contact angles of unmodified PEEK surface, modified PEEK surface by means of an exemplary method provided herein, and PEEK surface treated by means of another method.

FIG. 3 shows the zeta-potential variation versus pH of the electrolyte solution acquired from unmodified PEEK surface, modified PEEK surface by means of an exemplary method provided herein, and PEEK surface treated by means of another method.

FIG. 4 shows the proliferation statistics of BMSCs cultured on the sample surfaces obtained according to the modification process described in comparative example 1, comparative example 2 and example 1, and unmodified PEEK surface, wherein * and *** represent the statistically significant differences between two groups, * represents $p<0.05$, indicating a statistically significant difference exists between the two groups, and *** represents $p<0.001$, indicating a higher statistically significant difference exists between the two groups.

FIG. 5 shows ALP activity assay of the BMSCs cultured on the unmodified PEEK surface, the modified PEEK surface by means of a method provided herein, and the PEEK surface treated by means of another method for 14 days, wherein * indicates a statistically significant difference exists between the two groups.

In the FIGS. 6 to 14, unmodified PEEK, Ar-PIII treated PEEK, HF treated PEEK, and Ar-PIII and HF treated PEEK are designated as PEEK, A-PEEK, F-PEEK, and AF-PEEK, respectively.

Figure 6:
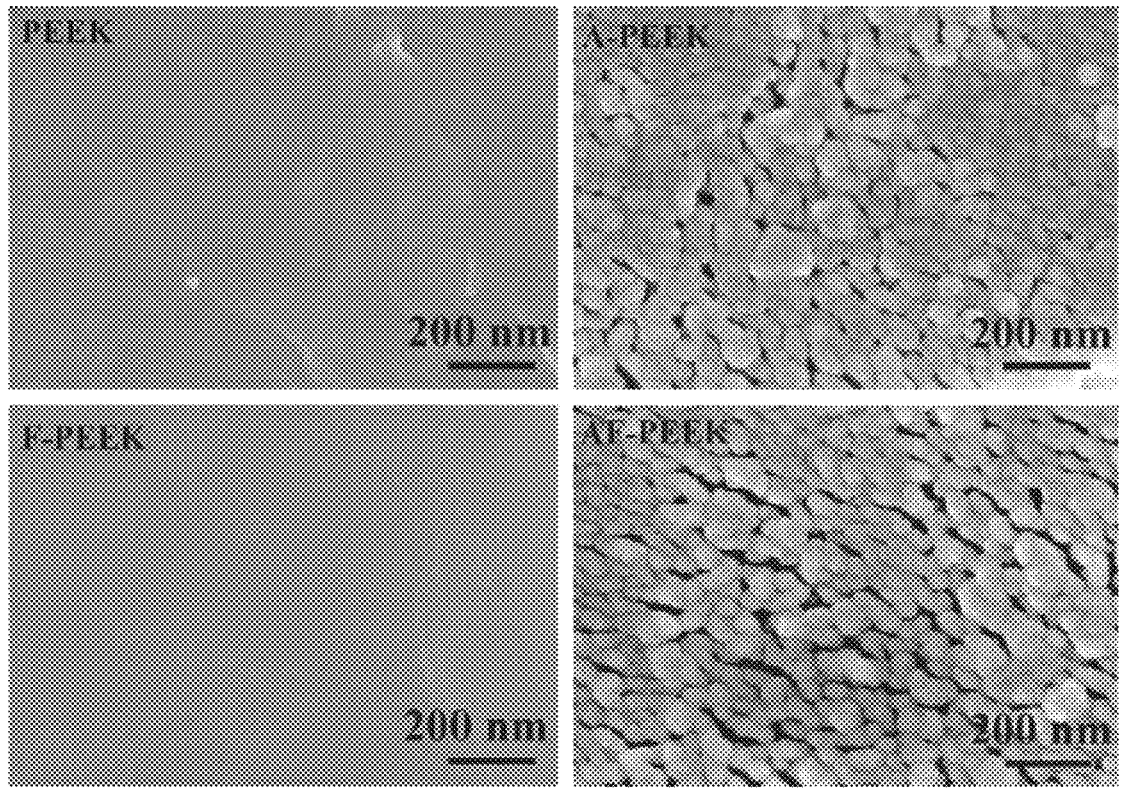

FIG. 6 shows the SEM morphologies of the unmodified PEEK surface, the modified PEEK surface by means of an exemplary method provided herein, and the PEEK surface treated by means of another method.

Figure 7A:
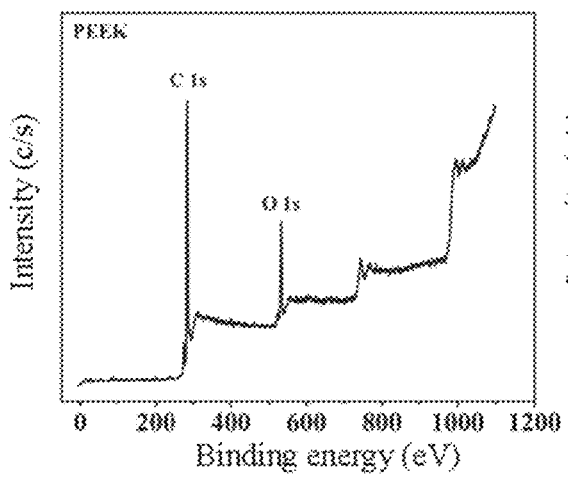
Figure 7B:
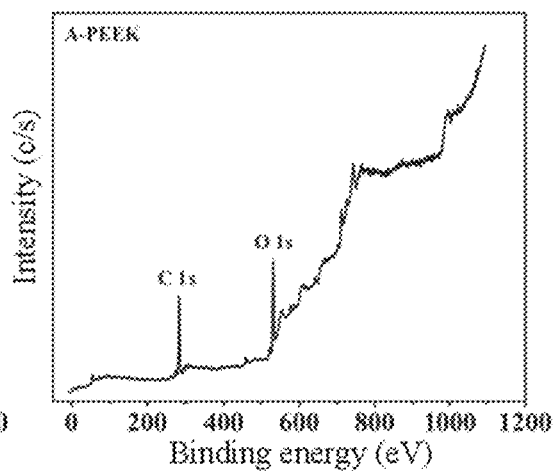
Figure 7C:
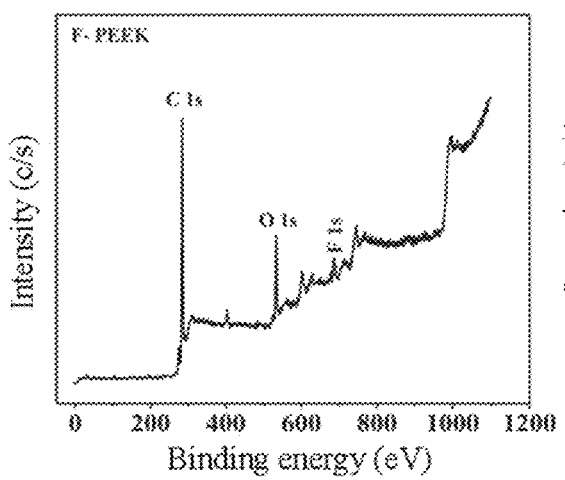
Figure 7D:
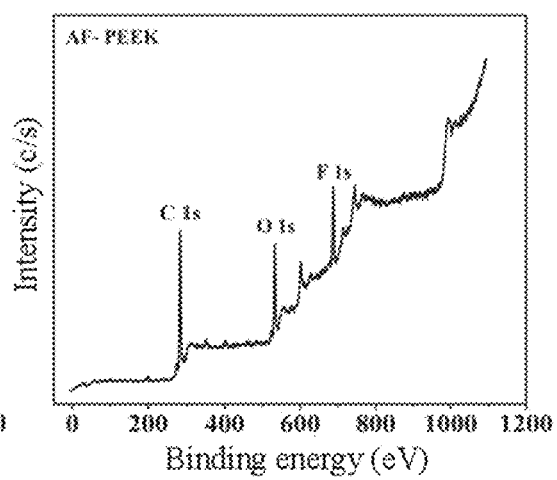

FIGS. 7A to 7D show the X-ray photoelectron spectroscopy (XPS) full spectra obtained from the unmodified PEEK surface, modified PEEK surface by means of an exemplary method provided herein, and PEEK surface treated by means of another method: FIG. 7A PEEK; FIG. 7B A-PEEK; FIG. 7C F-PEEK; and FIG. 7D AF-PEEK.

Figure 8:
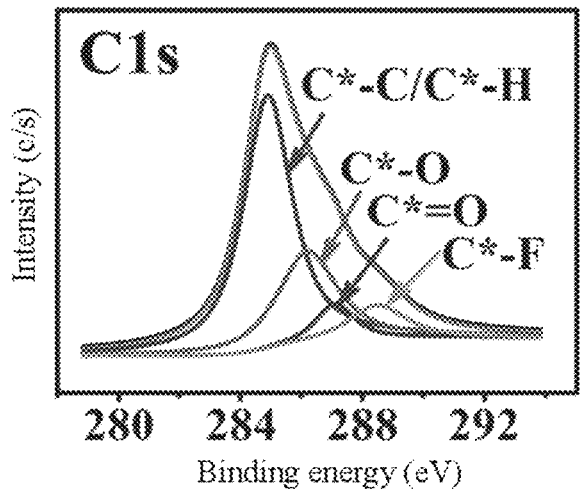

FIG. 8 shows the high-solution spectrum of C1s of AF-PEEK sample.

Figure 9:
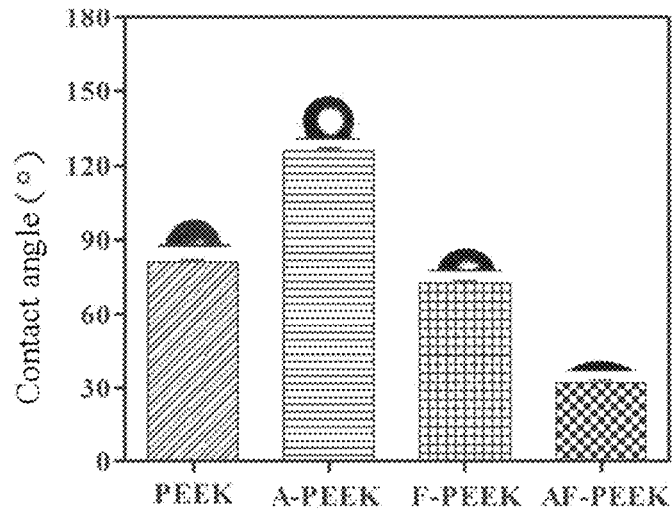

FIG. 9 shows the water contact angles of the unmodified PEEK surface, modified PEEK surface by means of an exemplary method provided herein, and PEEK surface treated by means of another method.

Figure 10:
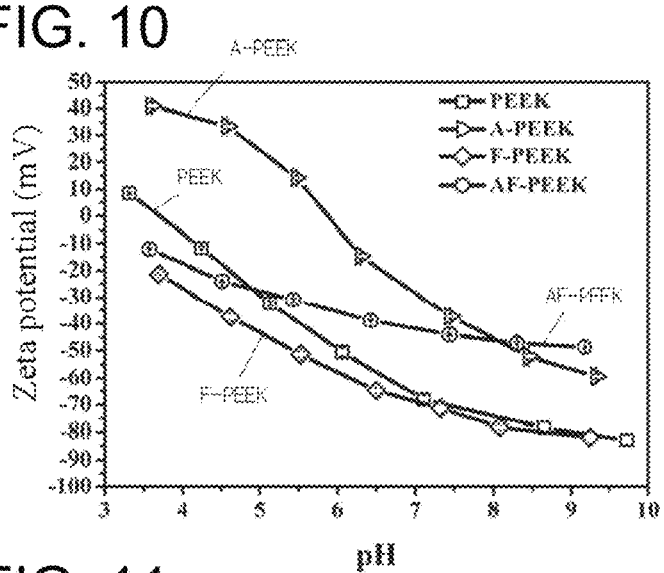

FIG. 10 shows the zeta-potential variation versus pH of the electrolyte solution acquired from the unmodified PEEK surface, modified PEEK surface by means of an exemplary method provided herein, and PEEK surface treated by means of another method.

Figure 11:
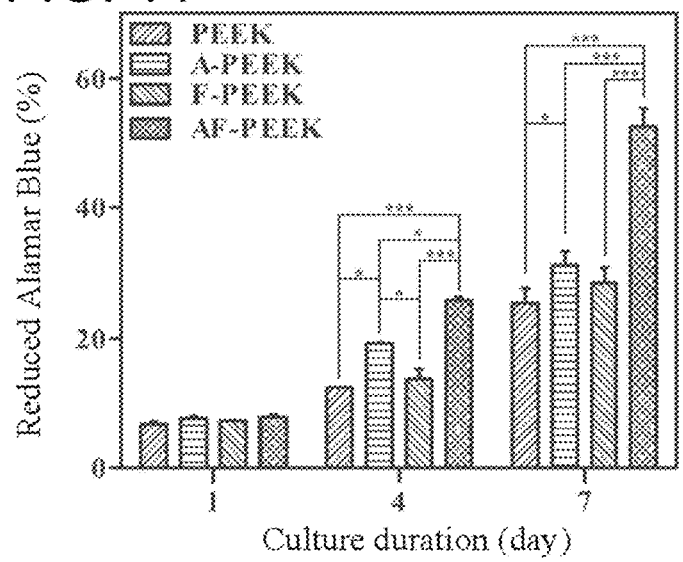

FIG. 11 shows the proliferation statistics of BMSCs cultured on the sample surfaces obtained according to the modification process described in comparative example 3, comparative example 4, and example 5, and the unmodified PEEK surface, wherein * and *** represent the statistically significant differences between two groups, * represents $p<0.05$, indicating a statistically significant difference exists between the two groups, and *** represents $p<0.001$, indicating a higher statistically significant difference exists between the two groups.

Figure 12:
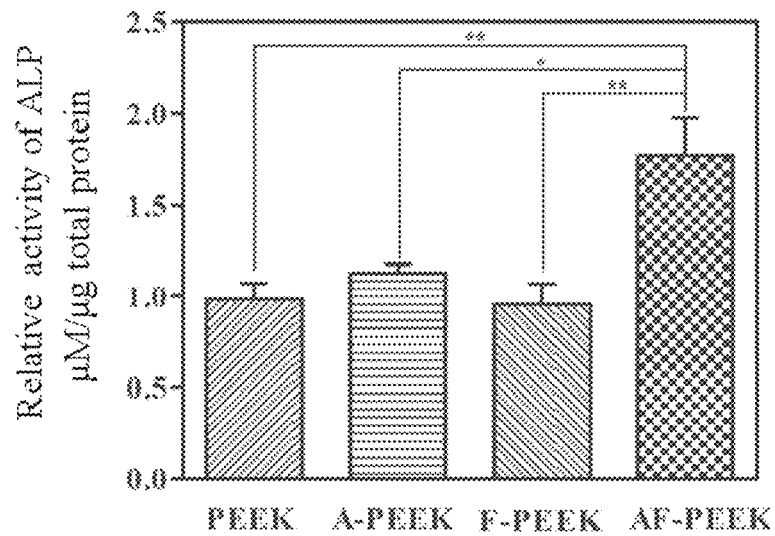

FIG. 12 shows ALP activity assay of the BMSCs cultured on the unmodified PEEK surface, the modified PEEK surface by means of an exemplary method provided herein, and the PEEK surface treated by means of another method for 14 days, wherein * and *** represent the statistically significant differences between two groups, * represents $p<0.05$, indicating a statistically significant difference exists between the two groups, and *** represents $p<0.001$, indicating a higher statistically significant difference exists between the two groups.

Figure 13:
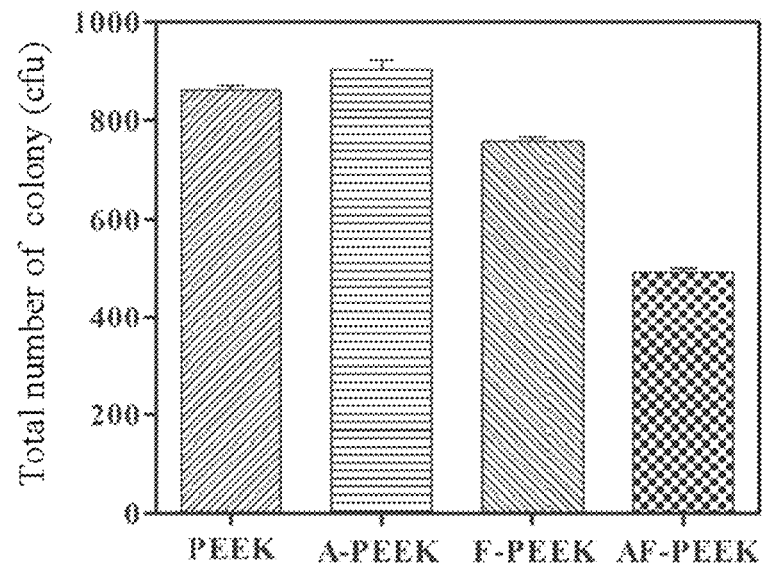

FIG. 13 shows the results of re-cultivated *Staphylococcus aureus* bacterial colonies on agar by the bacteria counting method from the unmodified PEEK surface, modified PEEK surface by means of an exemplary method provided herein, and PEEK surface treated by means of another method.

Figure 14:
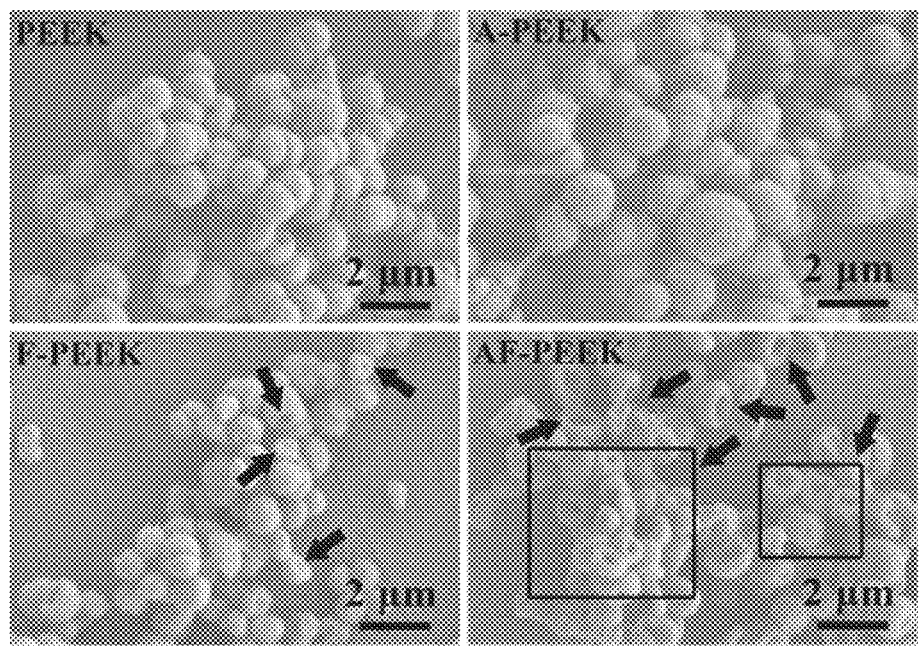

FIG. 14 shows SEM morphologies of *Staphylococcus aureus* bacteria cultured for 24 hours on the unmodified PEEK surface, modified PEEK surface by means of an exemplary method provided herein, and PEEK surface treated by means of another method.

DETAILED DESCRIPTION OF THE EMBODIMENTS

The present invention will be further described with the following embodiments below with reference to the drawings. It should be understood that the drawings and the following embodiments are only used for explaining this invention, and do not limit this invention. Any non-essential improvements and modifications made by a person skilled in the art based on this invention are all protected under the scope of this invention.

This invention aims to overcome the problems such as poor biocompatibility of medical PEEK material, and discloses a surface modification method for the PEEK material combining both plasma immersion ion implantation and chemical treatment techniques. The described method includes surface modifying PEEK using plasma immersion ion implantation with Ar plasma source, and immediately immersing the plasma modified PEEK material in the $H_2O_2$, HF, or $NH_3 \cdot H_2O$ aqueous solution. The PEEK surface modified according to this invention has nanoparticles, shallow nanoporous structures, and/or ravined nanostructures.

Due to its inherent chemical stability, PEEK possesses the ability to resist corrosion by most chemical reagents except concentrated sulfuric acid, which makes element introduction using a single chemical treatment difficult to achieve. However, some physical treatments, such as high-energy ion bombardment or implantation, are effective to surface modify an inert material surface. Therefore, this application provides a surface modification method combining both plasma immersion ion implantation and chemical treatment techniques, which first surface-activates the PEEK material using Ar plasma immersion ion implantation and then immediately immerses the PEEK material in a $H_2O_2$, HF, or $NH_3 \cdot H_2O$ aqueous solution for etching. Through this method, functional groups such as —OH, —F, or —$NH_2$ can be introduced onto the surface which will greatly enhance the biocompatibility and the antibacterial properties of the PEEK materials.

Hereinafter, the present invention will be better described with the following representative examples. It should be understood that the following examples are only used to explain this invention and do not limit the scope of this invention. Any non-essential improvements and modifications made by a person skilled in the art based on this invention are all protected under the scope of this invention. The specific parameters below such as temperature, time, and proportion are only exemplary, and a person skilled in the art can choose proper values within an appropriate range according to the description of this article, and are not restricted to the specific values cited below.

COMPARATIVE EXAMPLE 1

Square samples (10 mm×10 mm×1 mm) of pure polyether-ether-ketone (PEEK) were used. The samples were polished and ultrasonically cleaned in acetone (for 30 min) and ultra-pure water (for 30 min). The cleaned samples were dried in an air oven at a temperature of 80° C. and carefully preserved. Finally, the samples were treated using Ar plasma immersion ion implantation to give plasma modified PEEK (A-PEEK), and carefully preserved. Table 1 lists the specific parameters.

TABLE 1 parameters used in the Ar plasma immersion ion implantation

| | | | |
|---|---|---|---|
| Implantation voltage (V) | 800 | Argon flow (sccm) | 30 |
| RF power (W) | 300 | Background vacuum pressure (Pa) | $5 \times 10^{-3}$ |
| Duty ratio (%) | 30 | | |
| Implantation duration (min) | 60 | Frequency (kHz) | 30 |

Figure 1:
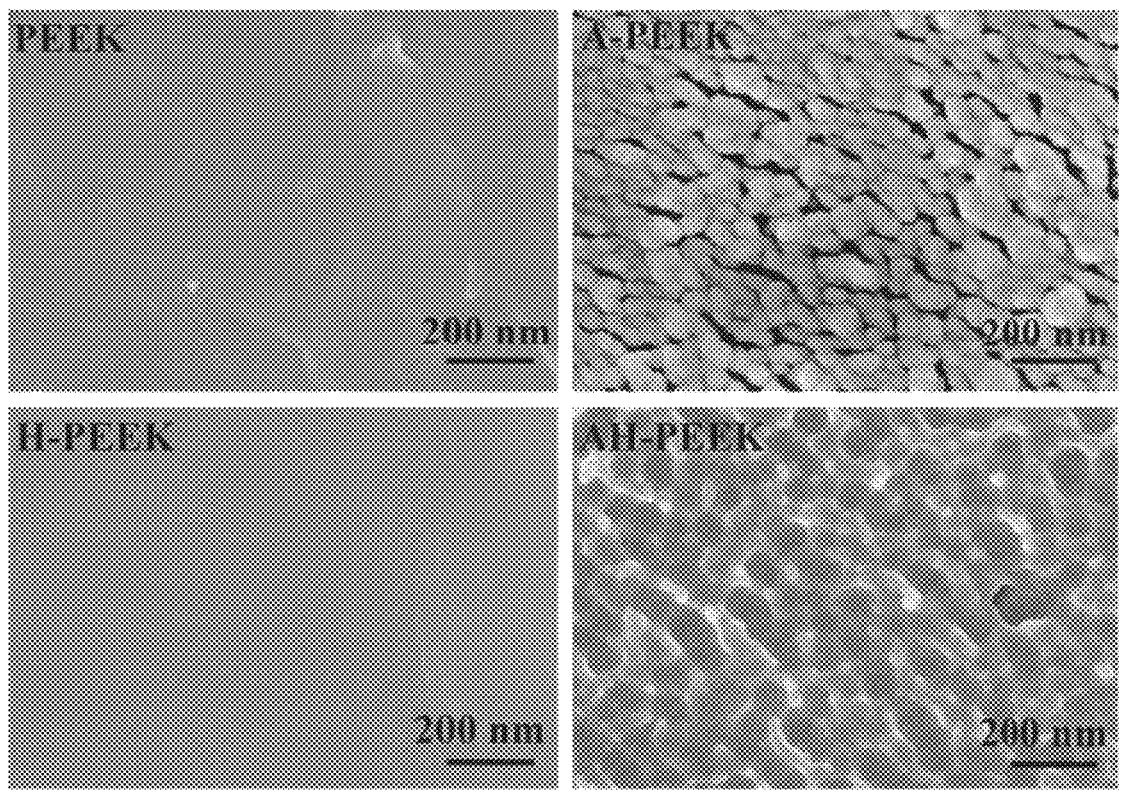
In FIGS. 1 to 5, unmodified PEEK, Ar-PIII treated PEEK, $H_2O_2$ treated PEEK, and Ar-PIII and $H_2O_2$ treated PEEK are designated as PEEK, A-PEEK, H-PEEK, and AH-PEEK, respectively.
Figure 2:
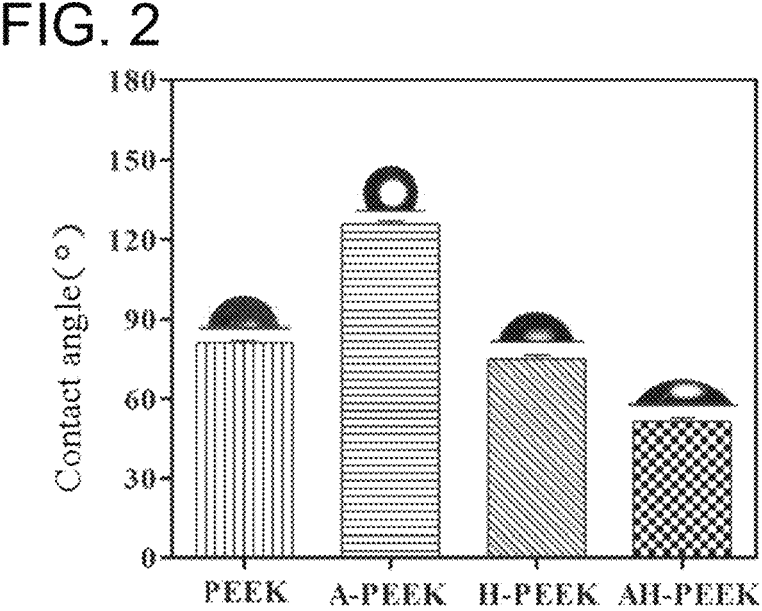

A-PEEK in FIG. 1 shows the SEM morphology of medical grade PEEK surface modified by means of the method from comparative example 1. It can be seen from the image that the ravined structure is formed on the modified surface with a size of several nanometers to a hundred nanometers, which is derived from the breaking molecular chain caused by a high-energy ion bombardment. The A-PEEK in FIG. 2 shows the water contact angle (126°) of the PEEK surface modified by means of the method from comparative example 1, indicating that the hydrophilicity of the PEEK surface is decreased with the formation of ravined structures due to the Ar-PIII treatment.

COMPARATIVE EXAMPLE 2

Square samples (10 mm×10 mm×1 mm) of pure polyether-ether-ketone (PEEK) were used. The samples were polished and ultrasonically cleaned in acetone (for 30 min) and ultra-pure water (for 30 min). The cleaned samples were dried in an air oven at a temperature of 80° C. and carefully preserved. Finally, the samples were immersed in 30 wt % $H_2O_2$ solution for 24 h, ultrasonically cleaned in distilled water (3 times, each time for 20 min), dried in air to give H-PEEK, and carefully preserved.

The H-PEEK in FIG. 1 shows the SEM morphology of a medical grade PEEK surface treated by means of the method from comparative example 2. It can be seen from the image that the treated surface is flat without structures and there is no obvious structural difference between PEEK and H-PEEK. The H-PEEK in FIG. 2 shows that the water contact angle (75°) of H-PEEK is similar to that (81°) of unmodified PEEK, indicating that the single $H_2O_2$ solution immersing treatment has no obvious effect on the morphology and the hydrophilicity of the PEEK material surface.

EXAMPLE 1

Square samples (10 mm×10 mm×1 mm) of pure polyether-ether-ketone (PEEK) were used. The samples were polished and ultrasonically cleaned in acetone (for 30 min) and ultra-pure water (for 30 min). The cleaned samples were dried in an air oven at a temperature of 80° C. and carefully preserved. The dried samples were treated using Ar plasma immersion ion implantation according to the process parameters listed in Table 1. Furthermore, the Ar-PIII treated samples were immediately immersed in an 30 wt % $H_2O_2$ solution for 24 h, ultrasonically cleaned in distilled water (3 times, each time for 20 min), dried in air to give AH-PEEK, and carefully preserved.

AH-PEEK in FIG. 1 shows the SEM morphology of the PEEK surface modified by means of the method from the example 1. It can be seen from the image that shallow nanoporous structures are formed on the modified surface with a size ranging from tens of nanometers to a hundred nanometers. AH-PEEK in FIG. 2 shows the water contact angle (51°) of the medical grade PEEK surface modified by means of the method from example 1, indicating that the hydrophilicity of PEEK is improved with the formation of the newly formed shallow nanoporous structures which is different from A-PEEK on the surface of PEEK due to the combination of the Ar-PIII treatment and the $H_2O_2$ solution immersing treatment.

EXAMPLE 2

The surface zeta-potential of samples treated according to comparative example 1, comparative example 2, and example 1 was measured to evaluate the electrical state of the surface. Specifically, the zeta-potential variation of the diffusion layer near the surface versus pH of the electrolyte solution was measured by a Surpass electrokinetic analyzer (Anton Parr, Austria). For each sample set, two specimens with a size of 20 mm×10 mm×1 mm were fixed face to face and parallel to each other on sample holders, with a certain gap between them. A KCl solution (0.001 M) was used as the electrolyte and the pH value thereof was adjusted by HCl and NaOH. At each pH value, the streaming current in the diffusion layer between the surface and the electrolyte, pressure, electrolyte constant, and size of the sample were measured, from which the zeta-potential was calculated using specific software. For statistical accountability, the zeta-potential was measured four times at each pH value.

Figure 3:
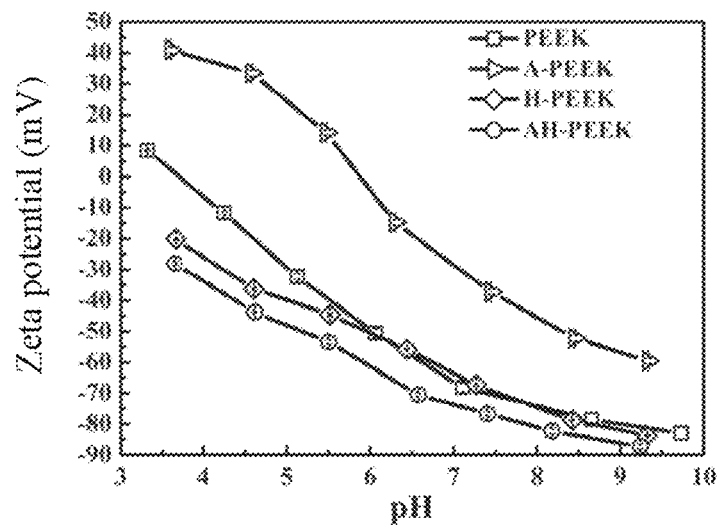

FIG. 3 shows the zeta-potential variation versus pH values for the modified PEEK surfaces obtained from the comparative examples and the examples above. All the curves reveal descending zeta-potential with the ascending pH values. Since the physiological environment has a pH value close to 7.4, the Zeta potential of material thereat is of much concern. From FIG. 3, at the pH value of 7.4, the zeta-potential values of PEEK and H-PEEK are almost the same. Compared with unmodified PEEK, A-PEEK shows a dramatically decreased absolute value of zeta-potential while AH-PEEK shows an increased absolute value of zeta-potential, which may be ascribed to the different surface structures after modification. The above data indicate that single $H_2O_2$ solution immersing treatment does not alter the electrical state near the PEEK surface while Ar-PIII treatment followed by $H_2O_2$ solution immersing treatment makes the PEEK surface have a higher absolute value of zeta-potential.

EXAMPLE 3

BMSCs were used to evaluate the cytocompatibility of the samples treated according to comparative example 1, comparative example 2, and example 1. The cell proliferation of BMSCs was determined using the alamarBlue™ assay (AbD serotec Ltd, UK). Detailed instructions are described as follows:

1) All the specimens were sterilized with 75% ethanol and transferred to 24-well tissue culture plates. 1 mL of BMSC suspension with a density of 2.0×10⁴ cell/mL was added to each well.

2) The 24-well tissue culture plates were incubated in an incubator with a humidified atmosphere of 5% $CO_2$ at 36.5° C. for 18 h.

3) After withdrawing the culture medium, the surface of the samples was cleaned by a phosphate buffer saline (PBS) solution. All the samples were transferred to a new 24-well tissue culture plate and incubated in the incubator.

4) After 1, 4, and 7 days, the culture medium was replaced by a fresh medium with 5% alamarBlue™ in each well. After incubation of the plates in the incubator for 4 h, 100 µL of the medium was transferred from each well to a 96-well plate.

5) The absorbance of each well at wavelengths of 570 nm and 600 nm was determined on an enzyme-labeling instrument (BIO-TEK, ELX 800) and the amount of reduced alamarBlue™ was calculated therefrom according to the following formula:

$$(111{,}216 \times A^{\lambda_1} - 80{,}586 \times A^{\lambda_2}) \div (155{,}677 \times A'^{\lambda_2} - 14{,}652 \times A'^{\lambda_1}) \times 100\%, \quad \text{Formula}$$

where A is the absorbance of the test wells; A' is the absorbance of negative control wells; $\lambda_1$=570 nm; and $\lambda_2$=600 nm.

Figure 4:
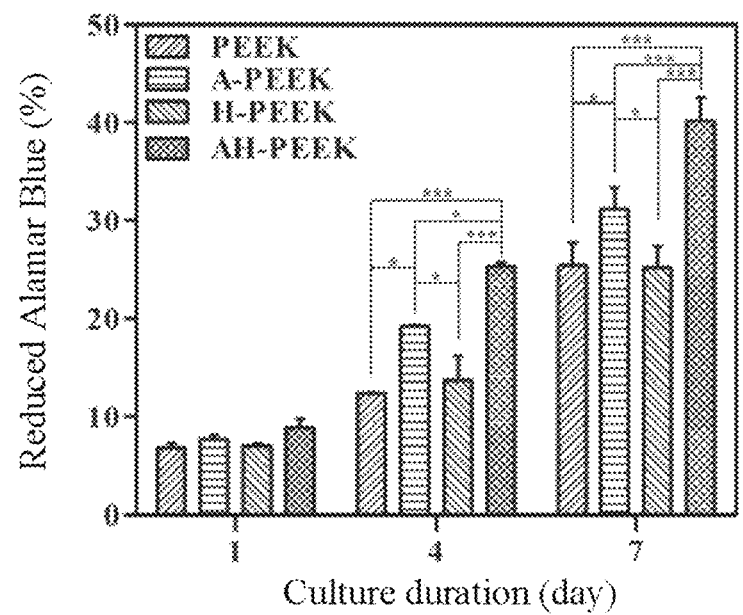

FIG. 4 shows the proliferation statistics of BMSCs cultured on the samples treated according to comparative example 1, comparative example 2, and example 1, and unmodified PEEK. It can be seen that cell proliferation on A-PEEK and AH-PEEK is significantly better than that on the unmodified PEEK, especially for the AH-PEEK. However, cell proliferation on H-PEEK has no obvious difference compared to that on the unmodified PEEK. It can be concluded that the shallow nanoporous structures can dramatically promote BMSC proliferation.

EXAMPLE 4

The ALP activity was detected after 14 days of incubation of BMSCs in vitro to further evaluate the cytocompatibility of the samples treated according to comparative example 1, comparative example 2, and example 1. Detailed instructions are described as follows:

1) All of the specimens were sterilized with 75% ethanol and transferred to 24-well tissue culture plates. 1 mL of BMSC suspension with a density of 2.0×10⁴ cell/mL was added to each well.

2) The 24-well tissue culture plates were incubated in an incubator with a humidified atmosphere of 5% $CO_2$ at 36.5° C. for 14 days. Culturing medium was replaced every 3 days.

3) At the given time of 14 days, all the samples were transferred to a new 24-well tissue culture plate. The surface of the samples was cleaned by a PBS solution. Afterwards, a lysis buffer was added to each well and kept at 4° C. for 40 min.

4) The cells were washed out of the samples and centrifuged, and the supernatant was decanted. The decanted supernatant, after the addition of p-nitrophenyl phosphate, was kept at 37° C. for 30 min, followed by an addition of a NaOH solution to stop the reaction. The absorbance of the solution at 570 nm was measured, from which the amount of p-nitrophenol generated was calculated.

5) A BCA protein method was employed to calculate the total protein content in the supernatant. The ALP activity was measured by the ratio of the molar amount of p-nitrophenol (µM) to the total protein content (µg).

Figure 5:
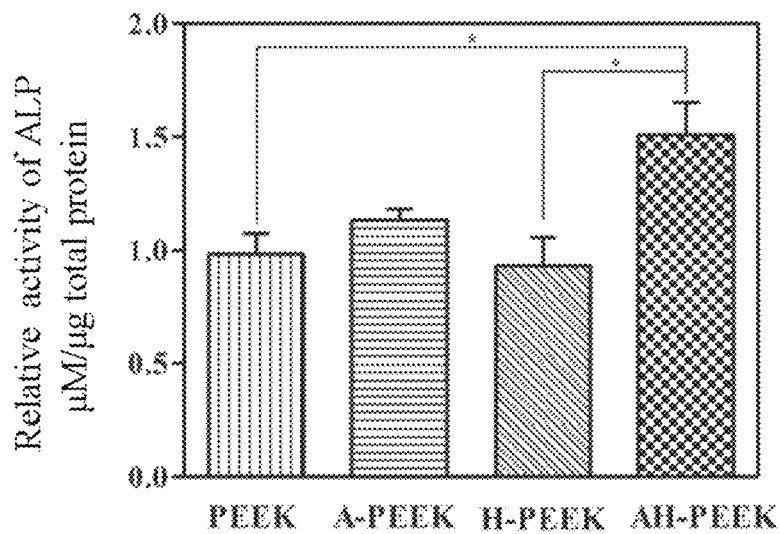

FIG. 5 shows the ALP activity assay result of the BMSCs cultured on the unmodified PEEK surface, the PEEK surface modified by means of the method provided herein, and the PEEK surface treated by means of another method for 14 days. It can be seen that the ALP activity of BMSCs cultured on samples of comparative example 1 and example 1 is higher than that on unmodified PEEK, especially for the sample of example 1. However, there is no significant difference of the ALP activity between samples of comparative example 2 and unmodified PEEK. It can be concluded that the shallow nanoporous structure on the surface of the PEEK obtained in example 1 can enhance the ALP activity of BMSCs. ALP is an early marker of osteogenic differentiation. Therefore, the shallow nanoporous structure can promote osteogenic differentiation of BMSCs, which is beneficial to enhance biocompatibility.

Through the above test results and further discussion, it can be concluded that a single $H_2O_2$ solution treatment has no obvious effect on the material and biological properties of the PEEK material, indicating this method is not effective to surface modify the PEEK material. However, a shallow nanoporous structure can form on the PEEK surface after the combination modification of Ar-PIII and following the $H_2O_2$ solution immersing treatment, which can greatly enhance the biological properties of the PEEK material. Therefore, this surface modification method is effective to the PEEK material, which also highlights the advantage of combining modification methods of both physical and chemical modification. In addition, a single Ar-PIII treatment has a certain modification effect but is less effective to the enhancement of the biological properties for the PEEK material, further confirming the superiority of combining modification methods of both physical and chemical modification.

COMPARATIVE EXAMPLE 3

Square samples (10 mm×10 mm×1 mm) of pure polyether-ether-ketone (PEEK) were used. The samples were polished and ultrasonically cleaned in acetone (for 30 min) and ultra-pure water (for 30 min). The cleaned samples were dried in an air oven at a temperature of 80° C. and carefully preserved. Finally, the samples were treated using Ar plasma immersion ion implantation to give modified PEEK (A-PEEK) and carefully preserved. Table 2 lists the specific parameters.

TABLE 2

| parameters used in the Ar plasma immersion ion implantation | | | |
|---|---|---|---|
| Implantation voltage (V) | 800 | Argon flow (sccm) | 30 |
| RF power (W) | 300 | Background vacuum pressure (Pa) | 5 × 10⁻³ |
| Duty ratio (%) | 30 | | |
| Implantation duration (min) | 60 | Frequency (kHz) | 30 |

A-PEEK in FIG. 6 shows the SEM morphology of the medical grade PEEK surface modified by means of the method from comparative example 3. It can be seen from the image that the ravined structure is formed on the modified surface with a size of several nanometers to a hundred nanometers, which is derived from the breaking molecular chain caused by a high-energy ion bombardment. A-PEEK in FIG. 9 shows the water contact angle (126°) of the PEEK surface modified by means of the method from comparative example 3, indicating that the hydrophilicity of the PEEK surface is decreased with the formation of the ravined structures due to the Ar-PIII treatment.

COMPARATIVE EXAMPLE 4

Square samples (10 mm×10 mm×1 mm) of pure polyether-ether-ketone (PEEK) were used. The samples were polished and ultrasonically cleaned in acetone (for 30 min) and ultra-pure water (for 30 min). The cleaned samples were dried in an air oven at a temperature of 80° C. and carefully preserved. Finally, the samples were immersed in a 40 wt % HF solution for 24 h, ultrasonically cleaned in distilled water (3 times, each time for 20 min), dried in air to give F-PEEK, and carefully preserved.

F-PEEK in FIG. 6 shows the SEM morphology of the medical grade PEEK surface modified by means of the method from comparative example 4. It can be seen from the image that the modified surface is flat without structures and there is no obvious structural difference between PEEK and F-PEEK. F-PEEK in FIG. 9 shows that the water contact angle (72°) of H-PEEK is similar to that of unmodified PEEK (81°), indicating that the single HF solution immersing treatment has no obvious effect on the morphology or the hydrophilicity of PEEK material.

EXAMPLE 5

Square samples (10 mm×10 mm×1 mm) of pure polyether-ether-ketone (PEEK) were used. The samples were polished and ultrasonically cleaned in acetone (for 30 min) and ultra-pure water (for 30 min). The cleaned samples were dried in an air oven at a temperature of 80° C. and carefully preserved. The dried samples were treated using the Ar plasma immersion ion implantation according to the process parameters listed in Table 2. Furthermore, the Ar-PIII treated samples were immediately immersed in a 40 wt % HF solution for 24 h, ultrasonically cleaned in distilled water (3 times, each time for 20 min), dried in air to give AF-PEEK, and carefully preserved.

AF-PEEK in FIG. 6 shows the SEM morphology of the medical grade PEEK surface modified by means of the method from the example 5. It can be seen from the image that a similar structure to A-PEEK was formed on the modified surface. AF-PEEK in FIG. 9 shows the water contact angle (32°) of the PEEK surface modified by means of the method from example 5. It can be seen that the surface structures of AF-PEEK is caused by the Ar-PIII treatment. The HF treatment will improve hydrophilicity but not alter the surface morphology.

EXAMPLE 6

The surface chemical states of the samples treated according to comparative example 3, comparative example 4, and example 5 were determined by X-ray photoelectron spectroscopy (XPS, Physical Electronic PHI 5000C ESCA System, updated by RBD corporation) equipped with a monochromatic MgKa source (with the range of 0~1256.3 eV), a high voltage of 14.0 kV, a power of 250 W, and a vacuum pressure below $1 \times 10^{-8}$ Torr. The full spectra at 0~1200 eV data (including high resolution spectra of C1s and O1s) were collected and analyzed using an RBD147 data acquisition card and AugerScan software.

FIG. 7 shows the XPS spectra obtained from the unmodified PEEK surface, the PEEK surface modified by means of the method provided herein, and the PEEK surface treated by means of another method. It can be seen that there is no other peak except a carbon (C1s) peak and an oxygen (O1s) peak detected on PEEK and A-PEEK, indicating that no impurity was introduced due to the Ar-PIII treatment. In addition, a significant peak representing fluorine (F1s) emerges in the spectrum of AF-PEEK at a binding energy of 687 eV, demonstrating that the sample surface is fluorinated. There is also a small peak of fluorine (F1s) in the spectrum of F-PEEK, and this may be due to the residual fluorine which is not cleaned out after the HF immersing treatment. According to the analysis of atomic percentage, the fluorine contents on the surface of F-PEEK and AF-PEEK are 0.79% and 9.01%, respectively, indicating that the fluorine on F-PEEK is much less than that on AF-PEEK and thus can be negligible. FIG. 8 is the high-resolution spectrum of carbon (C1s) on AF-PEEK, from which a fitted peak representing C*—F bond (288.5 eV) is clearly observed. Therefore, it can be concluded that fluorination of the PEEK surface is achieved through argon PIII followed by the HF immersing treatment, while the HF treatment alone can not fluorinate PEEK, indicating the important role of the Ar-PIII procedure in the fluorination and the activation effect of the Ar-PIII treatment.

EXAMPLE 7

The surface zeta-potential of samples treated according to comparative example 3, comparative example 4, and example 5 was measured to evaluate the electrical state of the surface. The testing procedure and conditions are described in example 2 (the PEEK materials obtained in comparative example 3, comparative example 4, and example 5 correspond to those obtained in comparative example 1, comparative example 2, and example 1, respectively, while other parameters and steps are the same as example 2).

FIG. 10 shows the zeta-potential variation versus pH values for the unmodified PEEK surface, modified PEEK surface by means of the method provided herein, and PEEK surface treated by means of another method. All the curves reveal descending zeta-potential with the ascending pH values. Since the physiological environment has a pH value close to 7.4, the Zeta potential of material thereat is of much concern. From FIG. 10, at the pH value of 7.4, the zeta-potential values of the four materials are all negative, and the zeta-potential value of F-PEEK is quite close to that of PEEK. After modification, the absolute values of zeta-potential of A-PEEK and AF-PEEK are both lower than that of PEEK, and this may be the result of the surface structure. Compared with A-PEEK, the zeta-potential of AF-PEEK is relatively more negative owing to the existence of fluorine in the surface. Test results indicate that, for PEEK material, the single HF solution immersing treatment will not alter the electrical state near the surface while the combination of the Ar-PIII treatment and the following HF solution immersing treatment greatly reduced the absolute value of zeta potentials.

EXAMPLE 8

BMSCs were used to evaluate the cytocompatibility of the samples treated according to comparative example 3, comparative example 4, and example 5. The cell proliferation of BMSCs was determined using the alamarBlue™ assay. Detailed instructions are described in example 4 (PEEK materials obtained in comparative example 3, comparative example 4, and example 5 correspond to those obtained in comparative example 1, comparative example 2, and example 1, respectively, while other parameters and steps are the same).

FIG. 11 shows the proliferation statistics of BMSCs cultured on the samples treated according to comparative example 3, comparative example 4, and example 5, and the unmodified PEEK. It can be seen that cell proliferation on A-PEEK and AF-PEEK is significantly better than that on the unmodified PEEK, especially for the AF-PEEK. However, cell proliferation on F-PEEK has no obvious difference compared to that on the unmodified PEEK. It can be concluded that the PEEK material obtained in example 5 can dramatically promote BMSC proliferation.

EXAMPLE 9

The ALP activity was detected after 14 days of incubation of BMSCs in vitro to further evaluate the bioactivity of the samples treated according to comparative example 3, comparative example 4, and example 5. Detailed instructions are described in example 4 (the PEEK materials obtained in comparative example 3, comparative example 4, and example 5 correspond to those obtained in comparative example 1, comparative example 2, and example 1, respectively, while other parameters and steps are the same).

FIG. 12 shows the ALP activity assay result of BMSCs cultured on the unmodified PEEK surface, modified PEEK surface by means of the method provided herein, and PEEK surface treated by means of another method for 14 days. It can be seen that ALP activity is up-regulated both on A-PEEK and AF-PEEK surface as compared with the unmodified PEEK surface, with AF-PEEK distinctly more positive for improving ALP activity. On the other hand, the ALP activity of BMSCs on F-PEEK is almost at the same level as PEEK, which confirms the surface of the PEEK material obtained in example 5 can improve the ALP activity of BMSCs. ALP is an early marker of osteogenic differentiation. Therefore, fluorination of the PEEK surface can promote osteogenic differentiation of BMSCs, which is beneficial to enhance the bioactivity.

EXAMPLE 10

The bacteriostatic activity of the samples treated according to comparative example 3, comparative example 4, and example 5 was evaluated using *Staphylococcus aureus* (*S. aureus*, ATCC 25923) by the method as follows. *S. aureus* were seeded on the surface of nutrient agar plates and cultured in an anaerobic incubator at 36.5° C. for 48 h, so as to be subcultured to the third generation to obtain pure *S. aureus* as the testing strains. The strains were scraped off, seeded on nutrient agar medium, and cultured for 24 h. The bacteria solution was diluted to $10^7$ cfu/mL with reference to standard bacterial turbidity tube. The specimens in 75% ethanol were shaken for 2 h to be sterilized, and then 60 μl of the bacteria solution was introduced onto each sample. After culturing in an anaerobic incubator with a humidity of 90% at 36.5° C. for 24 h, the bacteria was washed from the surface of all the samples by 4.5 mL of saline. The resulting bacteria suspension was diluted to a specified concentration. 100 μl of the diluted bacteria suspension was seeded onto a nutrient agar culture dish. After culturing in an anaerobic incubator at 36.5° C. for 24 h, the number of living bacterial colonies was recorded.

FIG. 13 shows the bacteria colony counting results of *S. aureus* cultured on the unmodified PEEK surface, the PEEK surface modified by means of the method provided herein, and the PEEK surface treated by means of another method. It can be found that the numbers of bacterial colonies on both F-PEEK and AF-PEEK surfaces are less than that on PEEK, while that on A-PEEK is more than that on PEEK. Setting pristine PEEK as reference, the percentage reduction of bacterial colonies on AF-PEEK calculated from the data of FIG. 13 is 42.89 (±2.06) %, indicating a fairish bacteriostatic effect. In comparison, the percentage reduction of bacterial colonies on F-PEEK calculated in the same way is 12.01 (±2.50) %, showing a very weak bacteriostatic effect which almost can be negligible, therefore, this PEEK material cannot meet the requirements of antibacterial materials.

EXAMPLE 11

The morphology of the *S. aureus* was examined using SEM observation to further evaluate the antibacterial activity of the samples treated according to comparative example 3, comparative example 4, and example 5. Specifically, 60 μl bacterial suspension of $10^7$ cfu/ml was seeded on each sample which has been sterilized in advance and then cultured in an anaerobic incubator with a humidity of 90% at 36.5° C. for 24 h. At the end of culturing, the samples were rinsed twice with PBS, transferred to a new 24-well plate, and fixed with 2.5% glutaraldehyde for 30 min. A series of ethanol solutions (30, 50, 75, 90, 95, 100 and 100% v/v) were used to dehydrate the samples sequentially. After the final dehydration the samples were successively put into a mixture of ethanol and hexamethyldisilazane (HMDS) (ethanol:HMDS=2:1, 1:1, 1:2 v/v) and a 100% HMDS solution for drying. Finally, the morphology of the bacteria was observed under SEM.

FIG. 14 shows the SEM morphologies of *S. aureus* seeded on the unmodified PEEK surface, the PEEK surface modified by means of the method provided herein, and PEEK surface treated by means of another method for 24 h. It can be seen that the *S. aureus* bacterial cells show intact surfaces and visible pseudopod on PEEK and A-PEEK, indicating good subsistence activity. There are a few bacterial cells exhibiting pitted surfaces on F-PEEK, while the number of pitted bacterial cells increases on AF-PEEK and most of them look more pitted or corrugated. This gives a hint of impeded bacterial survival on fluorinated PEEK surface, indicating fluorinated PEEK having a fairish bacteriostatic effect on *S. aureus*.

EXAMPLE 12

Square samples (10 mm×10 mm×1 mm) of pure polyether-ether-ketone (PEEK) were used. The samples were polished and ultrasonically cleaned in acetone (for 30 min) and ultra-pure water (for 30 min). The cleaned samples were dried in an air oven with a temperature of 80° C. and carefully preserved. The dried samples were treated using Ar plasma immersion ion implantation according to the process parameters listed in Table 1. Furthermore, the Ar-PIII treated samples were immediately immersed in a 25 wt % $NH_3H_2O$ solution for 24 h, ultrasonically cleaned in distilled water (3 times, each time for 20 min), dried in air, and carefully preserved. —$NH_2$ functional groups were formed on the PEEK surface.

In conclusion, there is no effect on the material and biological properties of PEEK material through the single HF solution treatment, indicating that the HF solution treatment is not effective to surface modify the PEEK material. However, fluorine can be introduced onto the PEEK surface through first the Ar-PIII treatment and following the HF solution immersing treatment, therefore greatly enhancing the biocompatibility and antibacterial activity of the PEEK material. It can be seen that the combination of physical and chemical treatment is advantageous and effective for PEEK surface modification. In addition, the single Ar-PIII treatment has a certain modification effect but is less effective to improve the biological properties of PEEK, which further confirms the advantage of the combination of physical and chemical treatment.

INDUSTRIAL APPLICATION

This invention is simple and controllable. Through the surface modification according to the methods of this invention, different nanostructures can be formed on the PEEK surface and the biocompatibility is greatly enhanced. There is also a potential application of the PEEK material in loading bone growth factor and antibacterial medicine, which will satisfy the clinical need of biomedical PEEK materials.

The invention claimed is:

1. A surface modification method for a polyether-ether-ketone material, which is a combination physical treatment and chemical treatment, the surface modification method comprising:
   a first step of performing plasma immersion ion implantation to effect the physical treatment on a surface of the polyether-ether-ketone material with an Ar plasma source to yield a plasma immersion ion implantation modified polyether-ether-ketone material; and
   a sequential second step of immersing the plasma immersion ion implantation modified polyether-ether-ketone material in a hydrofluoric acid aqueous solution for 6 to 24 hours to effect the chemical treatment by introducing fluorine to a surface of the plasma immersion ion implantation modified polyether-ether-ketone material, wherein
   a weight percentage of HF in the hydrofluoric acid aqueous solution is 20% to 40%,
   an atomic percentage of the fluorine concentration of the surface of the plasma immersion ion implantation modified polyether-ether-ketone material is 3.06% to 9.01%, and
   the combination of the physical treatment and the chemical treatment forms at least one of nanoparticles and nanopore structures in the surface of the plasma immersion ion implantation modified polyether-ether-ketone material.

2. The surface modification method according to claim 1, characterized in that the polyether-ether-ketone material is a pure polyether-ether-ketone material or carbon fiber reinforced polyether-ether-ketone material.

* * * * *